United States Patent
Choudhary et al.

(10) Patent No.: US 10,005,809 B2
(45) Date of Patent: Jun. 26, 2018

(54) BIO-ACTIVE ANTIOXIDANTS FROM PLANT FOODS FOR NUTRACEUTICAL PRODUCT DEVELOPMENT

(71) Applicants: M. Iqbal Choudhary, Karachi (PK); Juveria Siddiqui, Karachi (PK); Ahmed Abbaskhan, Karachi (PK); Suad Naheed, Karachi (PK); Achyut Adhikari, Karachi (PK); Jalauddine A. Jalal Awalia, Jeddah (SA)

(72) Inventors: M. Iqbal Choudhary, Karachi (PK); Juveria Siddiqui, Karachi (PK); Ahmed Abbaskhan, Karachi (PK); Suad Naheed, Karachi (PK); Achyut Adhikari, Karachi (PK); Jalauddine A. Jalal Awalia, Jeddah (SA)

(*) Notice: Subject to any disclaimer, the term of this patent is extended or adjusted under 35 U.S.C. 154(b) by 307 days.

(21) Appl. No.: 13/759,820

(22) Filed: Feb. 5, 2013

(65) Prior Publication Data

US 2014/0221634 A1    Aug. 7, 2014

(51) Int. Cl.
| | | |
|---|---|---|
| *C07H 17/065* | (2006.01) | |
| *C07H 17/075* | (2006.01) | |
| *A61K 31/7042* | (2006.01) | |
| *C07H 15/26* | (2006.01) | |

(52) U.S. Cl.
CPC ......... *C07H 15/26* (2013.01); *A61K 31/7042* (2013.01); *C07H 17/065* (2013.01); *C07H 17/075* (2013.01)

(58) Field of Classification Search
CPC ....... C07H 15/26; C07H 17/04–17/075; A61K 31/7042; A61K 31/7048
See application file for complete search history.

(56) References Cited

U.S. PATENT DOCUMENTS

2006/0088610 A1*  4/2006  Vorsa ........... A61K 31/353
                                              424/732

OTHER PUBLICATIONS

Chemical Abstracts Database, CAS Registry No. 1352618-04-2, entered on Jan. 9, 2012.*
Jordheim, M., Enerstvedt, K.H., Andersen, Ø.M. (2011) Journal of Agricultural and Food Chemistry, vol. 59, p. 7436-7440.*
Mesaik, M.A., Ahmed, A., Khalid, A.S., Jan, S., Siddiqui, A.A., Perveen, S., Azim, M.K. (Jan. 2013) Effect of Grewia Asiatica fruit on glycemic index and phagocytosis tested in healthy human subjects. Pakistan Journal of Pharmaceutical Sciences, vol. 26, No. 1, p. 85-89.*
Li, S. et al "The role of oxidative stress and oxidants in liver diseases" Int. J. Mol. Sci. (2015) vol. 16, pp. 26087-26124.*
Sharma, K. et al "Hepatoprotective efficacy of Grewia asiatica fruit . . . " Iran J. Radiat. Res. (2010) vol. 8, No. 2, pp. 75-85.*
Chi, C. et al "Hepatocyte growth factor gene therapy . . . " World J. Gastroenterol. (2005) vol. 11, No. 10, pp. 1496-1502.*
Nishguchi, S. et al "Prevention of hepatocellular carcinoma . . . " The Lancet (2001) vol. 357, pp. 196-197.*
Vernon, G. et al "Systematic review: the epidemology and natural history . . . " Aliment. Pharmacol. Ther. (2011) vol. 34, pp. 274-285.*

* cited by examiner

*Primary Examiner* — Leigh C Maier
(74) *Attorney, Agent, or Firm* — Sarfaraz K. Niazi

(57) ABSTRACT

The present invention relates to 5-O-[6"-(3-hydroxy-3-methyl glutarate)β-D-glucoside as a new antioxidant.

2 Claims, 3 Drawing Sheets

BIO-ACTIVE ANTIOXIDANTS FROM PLANT FOODS FOR NUTRACEUTICAL PRODUCT DEVELOPMENT

BACKGROUND OF THE INVENTION

Thirty one common fruit extracts were screened for their antioxidant potential by using $ABTS^{•+}$ and $DPPH^{•}$ radical scavenging assays and iron chelating capacity. Among them, the extract of *Grewia asiatica* L. (Phalsa) exhibited not only good in-vitro radical scavenging and iron chelating activity but also found to be good in in-vivo antioxidant and hepatoprotective activity by normalizing liver enzymes levels in animal model. Antioxidant-activity guided isolation of fruits of *G. asiatica* L., leads to the isolation of new compound, isorhamnetol 5-O-[6"-(3-hydroxy-3-methyl glutarate)]β-D-glucodise β-D-glucoside (1) in addition to kaempferol 3-O-β-D-glucoside (2), kaempferol 3-O-α-D-rhamnoside (3), quercetin 3-O-β-D-glucoside (4), quercetin 3-O-β-D-rhamnoside (5), quercetin 3-O-(2-p-courmaroylglucoside (6), myricetin 3-O-β-D-xyloside (7), 5-hydroxymethylfurfural (8), 3,4-dihydroxybenzoic acid (9), 1,5-dimethyl citrate (10), and trimethyl citrate (11). The structures of the isolated compounds were deduced by using mass spectrometry and 1D- and 2D-NMR techniques. Trolox equivalent antioxidant capacity (TEAC) measurements on compounds 1-11 were also carried out and potent antioxidant activity was observed.

The fruits of *Grewia asiatica* L., was identified as potential crop for nutraceutical products as number of bioactive compounds were identified and characterized. Further investigations are needed at molecular level to explore the mechanism of action of active ingredients.

SUMMARY OF THE INVENTION

An imbalance between the reactive oxygen species (ROS) and endogenous antioxidant defence is suggested to be a major cause of oxidative stress and ultimately the onset, of various diseases. There are varieties of antioxidant constituents present in human plasma including various classes of naturally occurring compounds, such as ascorbate, various proteins, thiols, bilirubin, urate and α-tocopherol. Diet based on plant-food is recommended due to rich source natural antioxidant compounds. Among the dietary antioxidants, naturally occurring flavonoids in plants have gained a significant recognition in the prevention of diseases and degenerative processes, associated with the oxidative stress. These include cancers, atherosclerosis, rheumatoid arthritis, aging and other clinical conditions associated with generalized leukocytes activation, such as shock, sepsis and trauma.

In subcontinent, squashes and traditional cold drinks, prepared from fruits of phalsa (*Grewia asiatica* L.) are amongst the most popular drinks in the summer seasons. The traditional uses of ripe fruits includes as cooling agent and tonic, for improving digestibility, quench thirst, against burning sensation and inflammation, heart and blood disorders, and fever. It is also good for the treatment of throat problems, and helps in the removal of dead fetus. The fruits of *G. asiatica* also find uses in folk cultures for the treatment of respiratory, cardiac and blood disorders, as well as for fever and inflammations. Some of the other medicinal properties of the barks of *G. asiatica* tree include demulcent and febrifuge effect whereas root bark is used for the treatment of rheumatism. The traditional application of the leaves of *G. asiatica* includes their use against skin eruptions due to its antibiotic properties. The extract of *G. asiatica* was found to have protective effects against radiation induced oxidative stress.

Pakistan has a tropical and sub-tropical climate which is suitable tor cultivation of fruits like phalsa (*Grewia asiatica* L.). It is, however, felt that phalsa has still not attracted attention of horticulturists to develop or introduce new cultivars that yield better quality of fruits with smaller stone and more flesh. If this is done it can open new vistas in food and beverage industries to step up their production, value addition, health food and nutraceutical production, both for domestic consumption and exports as well.

On the basis of in-vitro and in-vivo studies, *G. asiatica* was consequently subjected to characterize the compounds responsible of its antioxidant activities.

DETAILED DESCRIPTION OF THE INVENTION

Figure 1:
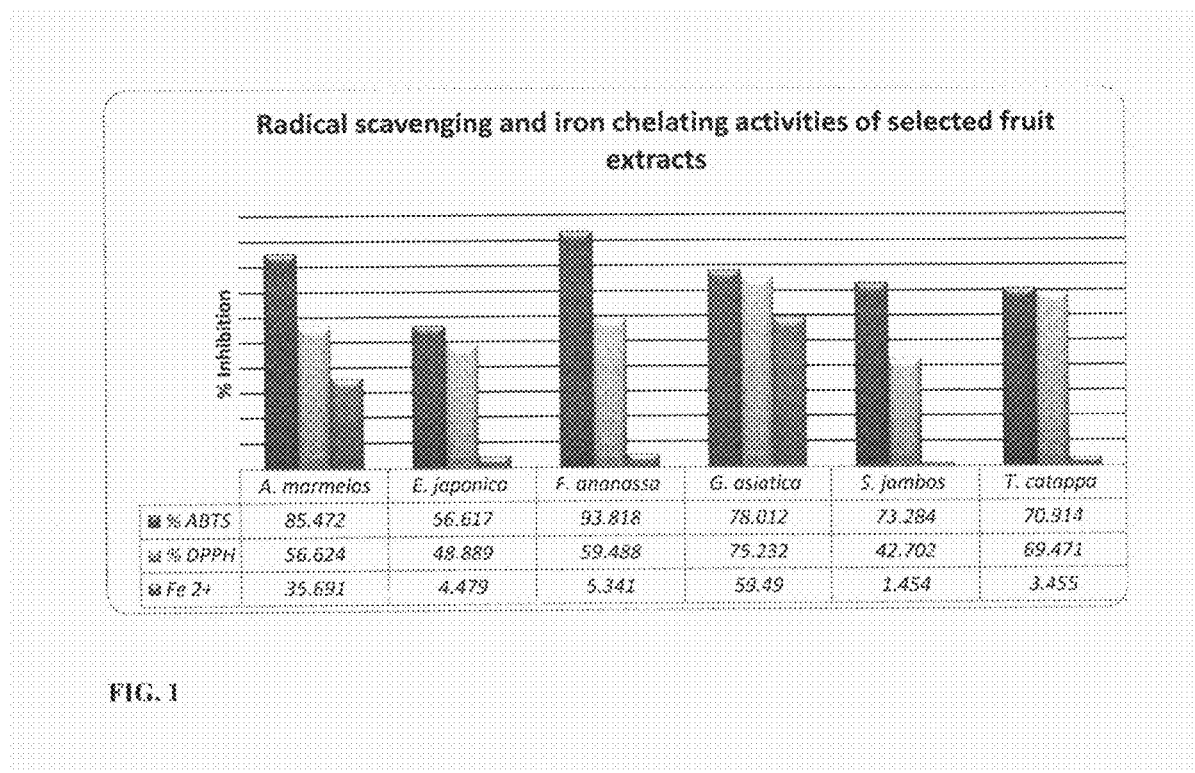
FIG. 1 depicts comparison of ABTS, DPPH radical scavenging, and $Fe^{2+}$ chelating activity of fruits extracts, at conc. 500 µg/mL, values expressed as mean µM±SEM, where n=3.

All chemicals, including standard compounds, were purchased from Sigma-Aldrich (St. Louis, USA). Buffers were prepared in distilled deionized water, obtained from Simplicity Water Purification System (Millipore, USA), HPLC grade ethanol (Merck, Germany) was used as solvent. All assays were performed by using 96-well microplates with Spectramax M2 spectrophotometer (Molecular Devices, CA, USA).

Fruit samples were purchased from the local vegetable market in Karachi. The botanical identification of the *G. asiatica* L. was performed by the Department of Botany, University of Karachi (Voucher no. 005, Herbarium No. 01570).

The edible part of all fruits were obtained by deseeding, peeling and cutting of the samples and then soaking in alcohol (5 L×3) for about two weeks at room temperature. The solvent was filtered and evaporated to obtain crude alcoholic extract for bioactivities.

The selected *G. asiatica* L. crude extract was partitioned, re-solubilized in water, and subsequently extracted with various organic solvents. Five major fractions, namely hexanes, dichloromethane, ethyl acetate, butanol and aqueous fraction were prepared.

DPPH Radical Scavenging Assay

The solution of $DPPH^{•}$ (1,1-diphenyl-2-pierylhydrazyl) was prepared by dissolving DPPH in ethanol (final concentration of 300 µM). [8] To the 96-well plate, 20 µL of sample (extracts/fractions, 500 µg/mL), control (solvent) and standard (1 mM Trolox, 6-hydroxy-2,5,7,8-tetramethylchroman-2-carboxylic acid) were added and the absorbance was recorded at 515 nm, 180 µL of prepared DPPH solution was then added and the plates were incubated for 30 min at 37° C. Decrease in absorbance, before and 30 mm after the addition of radical solution, was measured at 515 nm. The percentage of DPPH radical scavenging activity of extract or fractions was calculated by using following formula;

% Radical Scavenging Activity $(RSA)=100-(OD\ sample/OD\ control)\times100$ (1)

ABTS Radical Scavenging Assay

For ABTS radical scavenging assay, decrease in absorbance of preformed ABTS$^{•○}$ solution at 734 nm was recorded to evaluate the inhibition of radicals by active constitutes. Briefly, the reaction mixture or radical solution containing 1 mM ABTS (2-2'-Azinobis-3-ethylbenzthiazoline sulfonate), 35 µM $H_2O_2$, and 6 µM HRP in 0.7% acidified ethanol was prepared. The sample and radical solution were added in a similar manner as discussed earlier, while absorbance at 734 nm was recorded. The decrease in absorbance correlates with the inhibition of pre-formed radicals by antioxidant compounds present in the sample. Results were compared with the Trolox. Percent radical scavenging activity (% USA) was calculated by using Eq. 1.

Evaluation of Iron (II) Chelating Capacity Assay

The $Fe^{+2}$ chelating ability was determined according to the modified method described by Decker and Welch. The concentrations of $Fe^{+2}$ ions were measured from the formation of ferrous ion-ferrozine complex. In the 96-well plate, 5 µL (500 µg/mL) of selected extracts in pure DMSO (Dimethyl sulfoxide) was mixed with 35 µL of 0.0625 mM $FeCl_2$ (Ferrous chloride), and 60 µL of 4 mM ferrozine (reagents prepared in deionized distilled water). The mixture was shaken, and left at room temperature for 10 min. The absorbance of resulting mixture (100 µL, total volume) was measured at 562 nm. A lower absorbance of reaction mixture indicated a higher $Fe^{+2}$ chelating ability. Percent inhibition of absorbance was calculated according to the following formula;

% Inhibition=$100-(OD\ sample/OD\ control)\times100$ (2)

Animal Handling and Dosing Conditions

Male Wistar rats (average weight 120±20 g) were obtained from animal house facility of the ICCBS, University of Karachi. Rats were housed in polycarbonate cages, containing hardwood chip bedding. A standard pallet diet and water was made available ad-libitum. A 12 hr light/dark cycle was maintained throughout the study. After 14 days of acclimatization, the rats were randomized, and divided to 6 animals in each group: control, test, and positive control (Trolox). Oral doses of extracts were given after every alternate day and their physical status and weight changes were monitored daily. Control group has received an equal volume of normal saline for the same period of time. The experiment was terminated after two weeks of feeding. Under mild anesthetic conditions, blood was drawn via heart puncture. Blood was collected in clot activator plastic tubes, and allowed to clot for 30-40 minutes. Serum was separated by centrifugation and then stored at −20° C. till antioxidant status and other biochemical analysis were carried out.

Total Antioxidant Status (TAS)

The in-vivo antioxidant activity was evaluated by the method based on the method developed by Miller in 1993, using Randox Total Antioxidant Status assay kit with calibrator and controls (Randox Laboratories Ltd., Admore, UK) on 96-well plate.

LPT and Lipid Profile

The diagnostic facilities of PCMD (ICCBS), University of Karachi, were used for the biochemical analysis of serum samples. Lipid profile includes cholesterol, triglycerides, high density lipoproteins (HDL), low density lipoproteins (LDL), and LPT including bilirubin (total and direct), enzymes such as alanine aminotransferase (ALT), alkaline phosphatase (ALP), and gamma glutatmyltransferase (GGT), were measured. These assays were performed by fully automated chemistry analyzer (Hitachi 902, Roche Diagnostics, Japan) with standardized kits, calibrators, and controls. Total lipid was estimated manually by calorimetric method of phosphovanilline on a photometer (Clinicon 4010, Boehringer Meannheim, Germany).

Isolation of Bioactive Constituents

General Experimental

A variety of stationary and mobile phases were used to carry out isolation and purification of active metabolites. Stationary phase includes silica gel (E. Merck, type 60, 70-230, and 230-400 mesh), Sephadex LH-20 (Pharmacia, Uppsala, Sweden), ODS (reverse phase), polyamide, Diaion HP-20 resin, preparative TLC plates (20×20, 0.5 mm thick, $PF_{254}$ E. Merck). Recycling preparative HPLC (RP-HPLC) based separation was performed on a JAI LC-908W (Japan Analytical Industry, Japan), equipped with R1 and UV (256 nm) detectors, and ODS H-80, M-80 or L-80 stationary phases (YMC Co., Ltd., Japan). HPLC Grade methanol, acetonitrile and water from Merck were used as mobile phase. TLC Cards (pre-coated silica gel GF-255) were used for the detection purification, viewed at 254 nm under UV lights, and 366 nm for fluorescent spots. For staining TLC ceric sulphate reagent was sprayed, followed by heating.

Antioxidant Activity Guided and Isolation

ABTS$^{•+}$ radical scavenging activity guided isolation and purification of active metabolites was achieved using following procedures.

Well-matured G. asiatica fruits (20 Kg) were air-dried in shade and defatted by soaking in hexanes. Fruits were then soaked in alcohol (10 L×3) for about two weeks at room temperature. The solvent was filtered and evaporated to obtain crude alcoholic extract (1.2 Kg, 78.01% RSA). Crude extract was dissolved in distilled water and then partitioned with solvent mixture of increasing polarity in order to obtain fractions of hexanes (inactive), dichloromethane (75.4% RSA) ethyl acetate (82.4% RSA), butanol (86.% RSA), and water (87.4% RSA). Ethyl acetate, dichloromethane and aqueous fractions were further subjected to column chromatography for the purification of bioactive secondary metabolites. Dicholoromethane fraction (310 g) was subjected to silica gel column chromatography by using hexanes/DCM as elating solvent. A fraction obtained from 100% DCM (75.54% RSA) was further subjected to silica gel column chromatography with MeOH/DCM as elating solvents, which yielded compound 8. Ethyl acetate traction (220 g) was subjected to polyamide column chromatography by using MeOH/CHCl$_3$ as eluting solvent. Fraction obtained from 10% MeOH/CHCl$_3$ (87.93% RSA) when subjected to slica gel column with same eluting agent, yielded 9 sub-tractions. Sub-fraction 3, obtained from 3% MeOH/CH$_3$Cl$_3$ (88.77% RSA) was further subjected to PR HPLC by using L-80 column with 50% MeOH/H$_2$O, which yielded compound 9. Sub-fractions 5, obtained from 8% MeOH/CHCl$_3$ (89.37% RSA) were further subjected to PR HPLC by using ODS-M80 column with 3:1 H$_2$O/ACN, which yielded compounds 3-7.

Aqueous extract (200 g) was subjected to HP$_{20}$ column chromatography by using MeOH/H$_2$O which gives four sub-fractions. Sub-fraction obtained from 1:1 MeOH/H$_2$O, (80.50% RSA) was further subjected to LH$_{20}$ column chromatography, by using MeOH/H$_2$O as eluting solvent which yielded compound 11, and three sub-tractions. Sub-fraction, obtained from 100% MeOH (81.20% RSA) was further subjected to LH20 column chromatography. Sub-fraction obtained by 1:1 MeOH/H$_2$O (94.51% RSA) was subjected to repeated ODS polyamide column chromatography by using MeOH/CHCl$_3$ as eluting agent. Sub-fractions thus obtained from 20%, 40% and 80% MeOH/CHCl$_3$, were further subjected to PR HPLC by using ODS-L80 column with 1:1 MeOH/H$_2$O as eluting solvent, which yielded compounds 10 and 2 and 1 respectively.

Spectral Data of New Acylated Flavanoid Glycoside (Isorhamnetol 5-O-[6"-(3-hydroxy-3-methyl glutarate)] β-D-glucoside) (1)

Yellow amorphous powder UV (CH$_3$OH, nm) $\lambda_{max}$ (log ε): 354 (4.59), 273 (4.70), 257 (4.09), 208. IR (KBr, cm$^{-1}$) $\nu_{max}$:3390, 1724, 1648, 1643, 1516, 1510, and 1268, EI MS m/z: 622.1, HRFAB MS (+ve): m/z; 623.1620 (Calcd for C$_{28}$H$_{30}$O$_{16}$+H, 623.1612), FAB MS (+ve) m/z: 623 [M+H]$^+$, FAB MS (-ve) m/z: 621 [M-H]$^+$, for $^1$H-NMR (600 MHz CD$_3$OD) and $^{13}$C-NMR (125 MHz, CD$_3$OD) chemical shifts see Table 3.

TABLE 3

$^1$H- and $^{13}$C-NMR Chemical shift values of 1 (ppm, CD$_3$OD, 400 and 100 MHz respectively)

| Position | δ H (J = Hz) | δ C |
|---|---|---|
| Aglycone | | |
| 2 | — | 1 |
| 3 | — | 1 |
| 4 | — | 1 |
| 5 | — | 1 |
| 6 | 6.17 d (J$_{8, 6}$ = 1.8) | 1 |
| 7 | — | 1 |
| 8 | 6.38 d (J$_{6, 8}$ = 1.8) | 9 |
| 9 | — | 1 |
| 10 | — | 1 |
| 1' | — | 1 |
| 2' | 7.85 d (J$_{2', 6'}$ = 2.2) | 1 |
| 3' | — | 1 |
| 4' | — | 1 |
| 5' | 6.92 d (J$_{5', 6'}$ = 8.4) | 1 |
| 6' | 7.61 dd (J$_{6', 5'}$ = 8.4 and J$_{6', 2'}$ = 2.2) | 1 |
| Sugar | | |
| 1" | 5.21 d (J$_{1", 2"}$ = 8.0) | 1 |
| 2" | 3.34-3.50* | 7 |
| 3" | 3.34-3.50* | 7 |
| 4" | 3.34-3.50* | 7 |
| 5" | 3.34-3.50* | 7 |
| 6" | 4.13 bd (J$_{6"a, 6"b}$ = 10.5), 4.09 dd (J$_{6a", 6"b}$ = 10.5, J$_{6", 5"}$ = 3-OH, 3-CH$_3$ methyl glutaric | 6 |
| 1''' | — | 1 |
| 2''' | 2.24 d (J$_{2'''a, 2'''b}$ = 15.6), 2.30 d (J$_{2'''a, 2'''b}$ = 15.6) | 4 |
| 3''' | — | 7 |
| 4''' | 2.38 d (J$_{4'''a, 4'''b}$ = 14.2), 2.33 d (J$_{4'''a, 4'''b}$ = 14.2) | 4 |
| 5''' | — | 1 |
| 6''' | 1.15 s | 2 |
| OCH$_3$ | 3.94 s | 5 |

Assignments unclear due to overlapping, abbreviations: s; singlet, d; doublet; assignments confirmed by homonuclear decoupling, $^1$H—$^1$H COSY, NOESY, HMQC, and HMBC.

Trolox Equivalents Antioxidant Capacity (TEAC) Assay of Compounds (1-11)

Pure compounds and standards (conc. Range 10-1000 μM) were reacted with the fixed concentration of ABTS (0.5 mM) according to the reported method. [12] The decrease in absorbance at 734 nm was recorded 6 min after the addition of pro-formed ABTS radical solution. Standards including Trolox, quercetin, kaempferol and ascorbic acid were used for the comparison of structure-activity relationship with the isolated compounds. The calculation of TEAC values was obtained by plotting the graphs between various concentrations of compounds and percent radical scavenging activity. Slope (m) was then calculated by using the linear regression (y=mx+c) of the plotted curve. Ratio of the value of slope of Trolox with that of isolated compounds was calculated to get TEAC value as follows;

$$TEAC_{Compound} = \text{Slope of Trolox/Slope of compound} \quad (3)$$

Data Analysis

All the values are expressed as mean±SEM. Statistical analysis was carried out by using one-way ANOVA, followed by the Analysis of Variance. Statistical® (Version 5.0) software package was used for statistical analysis.

Results and Discussion

In-Vitro Radical Scavenging and Iron Chelating Potential of Fruits Extracts

Thirty one common fruits extracts were screened for their antioxidant activity using the DPPH˙ and ABTS˙+ radical scavenging assays (Table 1).

TABLE 1

ABTS*+ and DPPH* radical scavenging activity of fruits extracts

| S. No. | Botanical Name | English Name | % ABTS* | % DPPH* |
|---|---|---|---|---|
| | Achras zapota Linn. | Sapota | 16.89 ± 1.61 | N.D$ |
| | Aegle marmelos Linn. Correa. | Bael | 85.47 ± 0.78 | 56.62 ± 2.86 |
| | Ananas comosus L. Merr. | Pineapple | 8.28 ± 0.196 | 29.81 ± 2.65 |
| | Averrhoa carambola Linn. | Carambola | 67.32 ± 2.10 | 59.11 ± 213 |
| | Carica papaya Linn. | Papaya | 7.77 ± 1.32 | 4.23 ± 0.60 |
| | Carissa carandas Linn. | Karanda | 20.83 ± 1.21 | 52.97 ± 3.91 |
| | Citrullus lanatus Thunb. | Water Melon | 5.91 ± 0.44 | 6.92 ± 1.26 |
| | Citrus aurantifolia Christmann. | Lemon | 19.07 ± 3.21 | 15.83 ± 3.21 |
| | Citrus sinensis Linn. | Sweet Orange | 7.21 ± 1.56 | 8.31 ± 0.31 |
| | Cocos nucifera Linn. | Coconut | 1.47 ± 1.44 | 19.91 ± 5.32 |
| | Cucumis melo Linn. | Sweet Melon | 5.56 ± 0.52 | N.D$ |
| | Eriobotrya japonica Linn. | Loquat | 56.62 ± 1.72 | 48.89 ± 1.45 |
| | Fragaria ananassa Duch. | Strawberry | 93.82 ± 0.43 | 59.49 ± 2.86 |
| | Grewia asiatica Linn. | Phalsa | 78.01 ± 1.51 | 75.23 ± 0.82 |
| | Lichi chinensis Sonner. | Litchi | 9.20 ± 2.65 | 45.01 ± 2.10 |

TABLE 1-continued

ABTS*+ and DPPH* radical scavenging activity of fruits extracts

| S. No. | Botanical Name | English Name | % ABTS* | % DPPH* |
|---|---|---|---|---|
| | *Mangifera indica* Linn. | Mango | 25.92 ± 0.06 | 24.54 ± 1.21 |
| | *Malus sylvestris* Linn. | Apple | 8.62 ± 3.21 | N.D$ |
| | *Morus macroura* Miq. | Mulberry | 31.30 ± 0.39 | 26.11 ± 2.10 |
| | *Musa paradisica* Linn. | Banana | 19.84 ± 2.11 | 3.62 ± 1.78 |
| | *Opuntia vulgaris* Linn. | Prickly pear | 85.10 ± 0.035 | 14.42 ± 0.67 |
| | *Phoenix dactylifera* Linn. | Dates | 7.28 ± 0.35 | 1.48 ± 0.99 |
| | *Physalis peruviana* Linn. | Cape goose berry | 40.21 ± 1.21 | 49.17 ± 0.86 |
| | *Prunus armeniaca* Linn. | Apricot | 72.42 ± 0.87 | 15.58 ± 0.23 |
| | *Prunus avium* Linn. | Cherry | 20.93 ± 1.23 | 31.15 ± 1.45 |
| | *Prunus domestica* Linn. | Plum | 7.60 ± 0.62 | 18.16 ± 0.61 |
| | *Prunus persica* Linn. | Peach | 23.50 ± 0.98 | 14.55 ± 0.60 |
| | *Psidium guajava* Linn. | Guava | 38.27 ± 3.12 | 42.30 ± 1.20 |
| | *Syzygium jambos* L. Aisyon. | Jambul | 73.28 ± 1.46 | 42.70 ± 2.37 |
| | *Terminalia catappa* Linn. | Indian almond | 70.91 ± 0.39 | 69.47 ± 1.13 |
| | *Vitis vinifera* Linn. | Grapes | 69.42 ± 0.99 | 34.20 ± 1.21 |
| | *Zizyphus jujube* Linn. | Indian jujube | 19.85 ± 2.33 | 12.60 ± 2.15 |

Conc. of extracts, 500 μg/mL, values represent mean μM ± SEM (n = 3),
$not determined Moderate to good RSA were observed with a number of extracts, *Aegle marmelos, Eriobotrya japonica, Grewia asiatica, Syzygium jambos, Terminalia catappa* and *Fragaria ananassa* were found to have comparatively good activities and selected for further iron chelating potential evaluation. *G. asiatica, S. jambos*, and *T. catappa* were chosen for further in-vivo screening, as their $Fe^{+2}$ chelating potential was found to be highly significant (FIG. 1).

In-Vivo TAS and Biochemical Analysis of Selected Fruit Extracts and Fractions of *G. asiatica* L.

Figure 2:
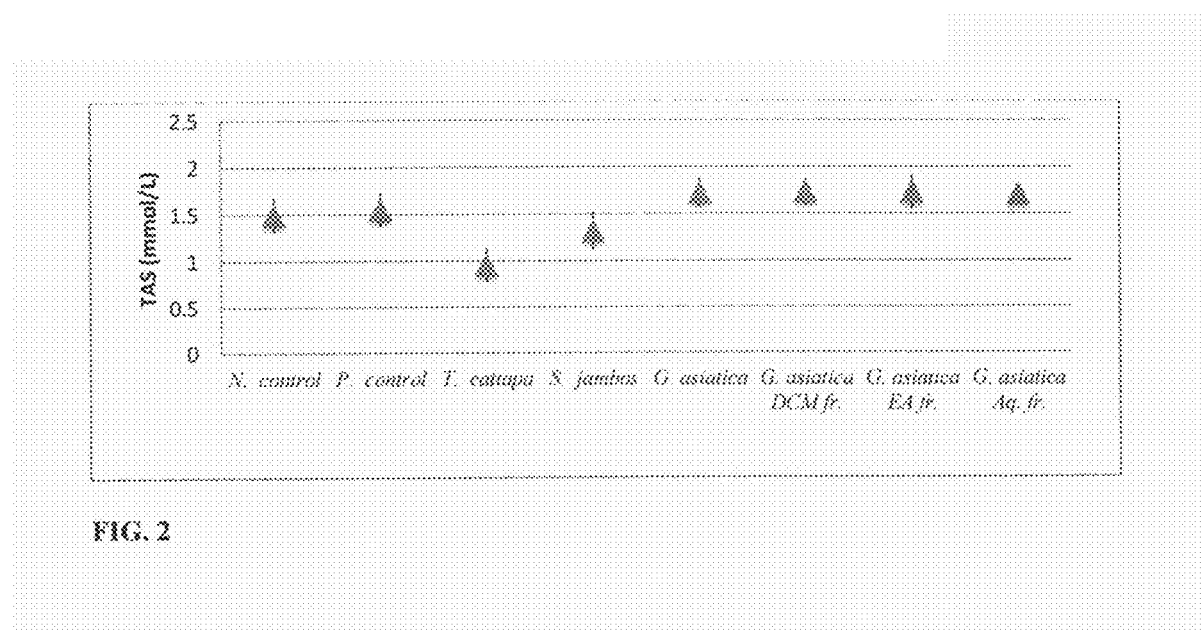
FIG. 2 depicts results of TAS (mmol/L) in animal oral dietary extract feeding experiment (100 mg/kg/body wt/day). Crude extracts and fractions of *G. asiatica* have higher antioxidant activities in-vivo, in comparison to normal and positive control (Trolox, 100 mg/kg/body wt/day).

The extracts which showed activities in various in-vitro antioxidant assays were evaluated for the in-vivo antioxidant activities by using normal animal model and results were compared with normal and positive control (Trolox treated). Among all selected samples for in-vivo assays, TAS of the crude alcoholic extract of *G. asiatica* showed the highest activity (FIG. 2). Four major fractions of *G. asiatica* were also subjected to in-vivo antioxidant activity measurement, and their effects on normal functioning of liver and lipid profile of animals were evaluated.

Figure 3:
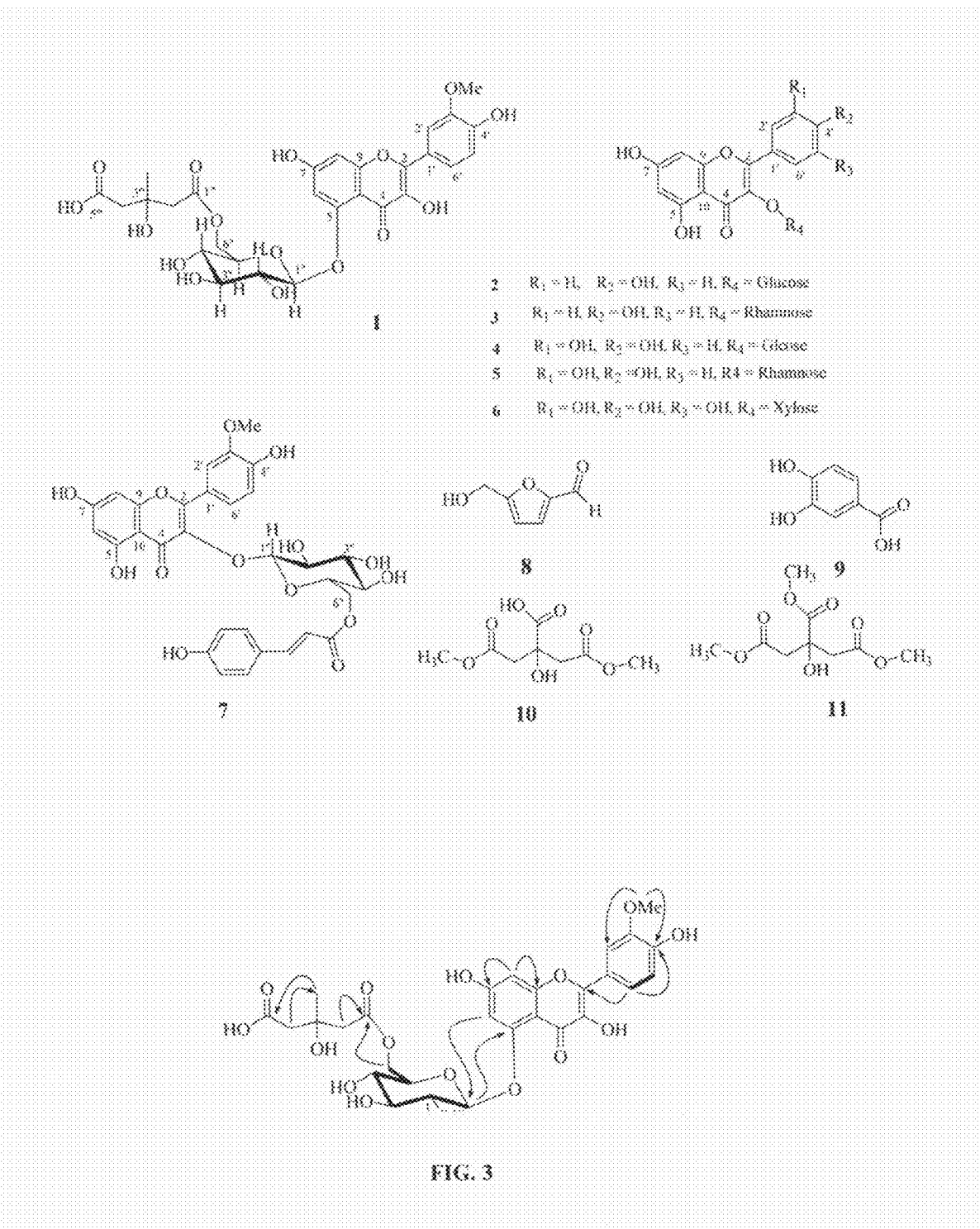
FIG. 3 depicts bioactive metabolites isolated from the fruits of *G. asiatica* L Key HMBC (—) correlations in compound 1.

The dichloromethane and aqueous fractions of *G. asiatica* were found to be potent in-vivo antioxidants, compared to positive control (FIG. 3). The results in current study showed normalising effects on enzymes and bilirubin levels in animal groups fed with various fractions of *G. asiatica*, as compared to positive control (Table 2).

TABLE 2

Effects of *G. asiatica* Sub-Fractions on liver function test (LFT) and lipid profile.

| | Normal control | Positive control | Crude ext. | Dichloromethane | Ethyl acetate | Aqueous |
|---|---|---|---|---|---|---|
| Total Lipid (mg/dL) | 213.25 ± 14.32 | 260 ± 5** | 267.5 ± 20.12* | 196.5 ± 4.09* | 206.5 ± 10.2* | 226.5 ± 13.38* |
| TAG (mg/dL) | 34.25 ± 3.34 | 40 ± 1.54** | 43.5 ± 2.25* | 38.7 ± 0.23* | 39.25 ± 5.89* | 40 ± 5.56* |
| Chol (mg/dL) | 46 ± 2.15 | 56.75 ± 2.07** | 60 ± 5.92* | 40 ± 1.54* | 41.50 ± 1.35* | 49.0 ± 1.87* |
| HDL-c (mg/dL) | 47 ± 1.77 | 55 ± 1.97** | 58 ± 5.68* | 37.0 ± 1.06* | 40 ± 1.22* | 47.5 ± 1.75* |
| LDL-c (mg/dL) | 11.25 ± 0.22 | 14.25 ± 0.96** | 14.5 ± 0.43* | 12.0 ± 0.94* | 11.25 ± 0.54* | 10.25 ± 1.14* |
| VLDL (mg/dL) | 7.5 ± 0.75 | 8.5 ± 0.25** | 8.75 ± 0.41* | 7.5 ± 0.25* | 8.25 ± 2.28* | 8.0 ± 0.94* |
| Total Bilirubin (mg/dl) | 0.432 ± 0.12 | 0.51 ± 0.02** | 0.45 ± 0.02* | 0.46 ± 0.01* | 0.45 ± 0.005* | 0.43 ± 0.02* |
| Direct Bilirubin (mg/dl) | 0.085 ± 0.006 | 0.085 ± 0.007** | 0.057 ± 0.004* | 0.035 ± 0.004* | 0.075 ± 0.01* | 0.052 ± 0.002* |
| Indirect Bilirubin (mg/dl) | 0.345 ± 0.01 | 0.43 ± 0.03** | 0.395 ± 0.02* | 0.43 ± 0.01* | 0.372 ± 0.01* | 0.38 ± 0.02 |
| ALT/SGPT (U/L) | 37 ± 0.71 | 45.5 ± 5.49** | 43.5 ± 5.55* | 41.5 ± 3.27* | 48 ± 2.89* | 46 ± 6.451* |
| ALP (U/L) | 117 ± 5.23 | 212.54 ± 24.51** | 159.75 ± 15.25* | 180.25 ± 16.27* | 192 ± 5.84* | 151.5 ± 9.93* |
| GGT (U/L) | 3 ± 0.61 | 4.25 ± 0.74 | 2.75 ± 0.41* | 2.25 ± 0.21* | 3.25 ± 0.44 | 2.5 ± 0.25 |

Results expressed as mean mg/dL or U/L ± SEM, where n = 6,
**$P < 0.05$: Normal control v/s positive control,
*$P < 0.05$: Normal control v/s *G. asiatica* extract and fractions (ANOVA)

This suggested that various fractions of G. asiatica possess hepatoprotective effect, causing a lowering of the liver enzymes (ALT, ALP, GGT), and bilirubin levels. The study showed that compounds present in the fractions of G. asiatica have a potential to protect liver. The results are in accordance with the earlier reports on other natural products.

Structure Elucidation of Compounds

A combination of column chromatography using size exclusion, normal phase and reverse phase adsorbents, were employed to isolate of thirteen compounds from ethyl acetate and aqueous extracts. Compound 1 was isolated as yellow powder. The molecular formula was determined to be $C_{28}H_{30}O_{16}$ from HRFAB-MS (+ve) as it showed $[M+H]^+$ m/z 623.1620 (Calcd for $C_{28}H_{30}O_{16}+H$, 623.1612), $^{13}C$- and $^1H$-NMR spectra displayed five downfield methine signals at $\delta_C/\delta_H$ 100.8/6.17 d (1H, $J_{6,8}$=1.8 Hz), 95.5/6.38 d (1H, $J_{8,6}$=1.8 Hz), 116.9/6.92 d (1H, $J_{5',6'}$=8.4 Hz), 123.5/7.61 dd (1H, $J_{6',5'}$=8.4 Hz, $J_{6,2'}$=2.2 Hz), and 114.5/7.85 d (1H, $J_{2',6'}$=2.2 Hz), which were assigned to the C-6, C-8, C-6', C-5' and C-2' methane carbons respectively. $^{13}C$- and $^1H$-NMR spectrum indicated the presence of a sugar molecule in compound by showing resonances at $\delta_C/\delta_H$ 104.3/5.21 d (1H, $J_{1'',2''}$=8.0 Hz, CH-1''), 75.5/3.45 overlapped (1H, CH-2''), 71.1/3.41 overlapped (1H, CH-3''), 75.8/3.40 overlapped (1H, CH-4''), 78.0/3.35 overlapped (1H, CH-5''), and 64.1/4.13 br d (1H, $J_{6'',5''}$=10.5 Hz,)/4.09 dd (1H, $J_{6a'',6b''}$=10.5 Hz, $J_{6'',5''}$=4.5 Hz, $CH_2$-6''). A couple of cross-peaks in the HMBC spectrum between H-1'' ($\delta_H$ 5.21)/C-5 ($\delta_C$ 161.8), and H-6 (($\delta_H$ 6.17)/C-1'' (($\delta_C$ 104.3) indicated that β-D-glucopyranoside is substituted at C-5 of the flavonoid skeleton. The HMBC correlation between $\delta_H$ 3.94 (OMe), and $\delta_C$ 148.3 (C-3'') indicated the position of the —OMe group at C-3''. Anomeric proton appeared as a doublet at $\delta_H$ 5.21 (d, J=8.0 Hz), which indicated a β-linkage of the sugar moiety. Moreover, the $^1H$-NMR spectrum also showed AB geminal protons resonated at δ2.24 (d, $J_{2''a,2''b}$=15.6 Hz), and 2.30 ($J_{2''a,2''b}$=15.6 Hz), while another AB doublets ascribed to the $H_2$-2'', while resonances at δ2.33 ($J_{4'''a,4'''b}$=14.2 Hz) and 2.38 ($J_{4'''a,4'''b}$=14.2 Hz), which were attributed to the $H_2$-4'''.

Further analysis of the 1D- and 2D-NMR data supported the presence of a hemiterpene unit (3-hydroxy-3-methylglutaric acid) in compound 1, which was found to be substituted with a C-6'' of β-D-glucopyranoside, based on the HMBC correlations. Key HMBC Interactions in compound 1 are shown in FIG. 3. $^{13}C$-NMR Chemical shifts values of sugar moiety of compound 1 were in accordance with the reported $^{13}C$-NMR values for D-glucose. The stereochemistry at C-3 was deduced by comparasion with the reported spectroscopic data of the same moiety. From the spectral data, the structure of compound 1 was deduced as isorhamnetol 5-O-[6''-(3-hydroxy-3-methyl glutarate)] β-D-glucoside.

The structures of known, compounds were determined by comparing spectral data with the reported literatures and identified as kaempferol 3-O-β-D-glucoside (2), kaempferol 3-O-β-D-rhamnoside (3), quercetin 3-O-β-D-glucoside (4), quercetin 3-O-β-D-rhamnoside (5), quercetin 3-O-(2-p-coumaroylglucoside) (6), myricetin 3-O-β-D-xyloside (7), 5-hydroxymethylfurfural (8), 3,4-dihydroxybenzoic acid (9), 1,5-dimethyl citrate (10), trimethyl citrate (11). Among them, except compounds 2 and 4 all others were obtained for the first time from this plant.

Structure-Antioxidant Activity Relationship of Isolated Constituents

The TEAC assay was used to assess the power of reduction of total amount of $ABTS^{•+}$ radicals formed during the reaction by bioactive metaboilte. The ABTS is intensely colored and when it reacts with antioxidant the color disappeared. The TEAC value therefore shows the capacity of a test compound to donate hydrogen and scavenge preformed $ABTS^{•\circ}$ radical cation. In present procedure, the ratio of the slope of concentrations of standard and test compound is taken, therefore TEAC is considered as relative value with no unit. Trolox used as standard antioxidant with TEAC value as 1.

The 3-OH group with the contiguous double bond in the C-ring consisted to be as radical stabilizer in quercetin (TEAC=1.07±0.23). Glycosylation at C-3 reduces the delocolization, of electron in compounds 3 and 4, but the C-3' and C-4'-hydroxylation still lead to the higher TEAC values 0.82±0.32 and 0.82±0.23, respectively (Table-4).

TABLE 4

The Antioxidant Activities of Isolated Compounds of Grewia asiatica L.

| No | Samples | $TEAC^a$ ± SEM |
|---|---|---|
| 1 | Isorhamnetol 5-O-[6''-(3-hydroxy-3-methyl glutarate)] β-D-glucoside (1) | 0.88 ± 0.21 |
| 2 | Kaempferol 3-O-β-D-glucopyranoside (2) | 0.80 ± 0.31 |
| 3 | Kaempferol 3-O-β-rhamnpyrnoside (3) | 0.91 ± 0.21 |
| 4 | Quercetin 3-glucoside (4) | 0.82 ± 0.32 |
| 5 | Quercetin 3-rhamnoside (5) | 0.82 ± 0.23 |
| 6 | Quercetin 3-O-β-D-2-p-coumaroylglucoside (7) | 0.36 ± 0.19 |
| 7 | Myricetin 3-O-β-D-xyloside (6) | 0.92 ± 0.35 |
| 8 | 3,4-Dihydroxybenzoic acid (8) | 1.05 ± 0.24 |
| 9 | 5-Hydroxymethylfurfural (9) | 0.95 ± 0.01 |
| 10 | 1,5-Dimethyl citrate (10) | 0.67 ± 0.31 |
| 11 | Trimethyl citrate (11) | 0.58 ± 0.12 |
| 12 | Quercetin (reference) | 1.07 ± 0.23 |
| 13 | Kaempferol (reference) | 0.97 ± 0.27 |
| 14 | Ascorbic acid (reference) | 1.14 ± 0.29 |
| 15 | Trolox (reference) | 1 |

$^a$TEAC: Trolox equivalent antioxidant capacity, values represent mean ± SEM (n = 3)

The comparison of quercetin with kaempferol (Table-4) indicated the importance of two adjacent hydroxyl groups in the ring B of quercetin. The C-2/C-3 double bond, and 3-OH groups of keampferol appear to be the major contributor in activity (TEAC 0.97=0.27). Additional third hydroxyl group does not enhances the antioxidant potential in ring B of myricetin when compared, with quercetin (TEAC 0.92±0.35) (Table-4). The results in current study are in accordance with the already established radical stabilization effects of flavonoids. The unsaturation in ring C allows the electron delocalization across the molecule for die stabilization of the aryloxyl radicals.

Oxygen in furan ring, aldehyde oxygen adjacent to C-1/C-3, and C-4/C-3 double bonds conjugated system makes 5-hydroxymethyl furfural (8) an excellent candidate for radical stabilization effect with highest TEAC value (1.05±0.24), among all isolated compounds (Table-4). In addition to flavanoid glycosides, 5-hydroxymethyl furfural (8) is the most potent compound obtained from G. asiatica fruit extract. Various bioactivities of this compound have also been reported.

The hydroxy substituents of 3,4-dihyroxybenzoic acid (9) cause the antioxidant activity. The meta and para hydroxylation on ring A influence the electron withdrawing capacity (Table-4).

Citric acid derivatives (10 and 11) showed moderate to low antioxidant activity. Carboxylic acid group of citric acid is replaced with methyl groups at C-1 and C-5 in 1.

5-dimethyl citrate (10), and at C-1, C-5 and C-6 in trimethyl citrate (11), respectively (TEAC 0.67±0.31, 0.58±0.12) (Table-4).

The study of natural products for their therapeutic potential has led to the development of many new drugs as well as functional foods. Particularly important are the dietary plants which can serve as functional foods and nutraceuticals to prevent diseases and promote health. The development of new antioxidant supplements, functional ingredients and products should be based on well-defined and systematic screenings against valid therapeutic targets.

What is claimed is:

1. A method of reducing oxidative stress to liver by administering to those in need of treatment a suitable quantity of pure isorhamnetol 5-O-[6"-(3-hydroxy-3-methyl glutarate)]-β-glucoside, or a stereoisomer, a pharmaceutically acceptable salt, ester or solvate thereof and further comprising suitable pharmaceutical ingredients for oral delivery of isorhamnetol 5-O-[6"-(3-hydroxy-3-methyl glutarate)]-β-glucoside into body.

2. The method according to claim 1 of reducing oxidative stress to liver, wherein oxidative stress causes elevation of liver enzymes.

* * * * *